United States Patent [19]

Carrico et al.

[11] Patent Number: 4,806,631

[45] Date of Patent: Feb. 21, 1989

[54] IMMOBILIZATION OF NUCLEIC ACIDS ON SOLVOLYZED NYLON SUPPORTS

[75] Inventors: Robert J. Carrico; Robert P. Hatch; William L. Patterson, all of Elkhart, Ind.

[73] Assignee: Miles Inc., Elkhart, Ind.

[21] Appl. No.: 781,514

[22] Filed: Sep. 30, 1985

[51] Int. Cl.[4] .................... C07H 21/00; C12Q 1/68
[52] U.S. Cl. ........................ 536/27; 935/78; 435/6; 435/803
[58] Field of Search ............ 935/78; 436/501; 435/6, 435/803, 7; 536/27

[56] References Cited

U.S. PATENT DOCUMENTS

| | | | |
|---|---|---|---|
| 4,298,685 | 11/1981 | Parikh et al. | 435/7 |
| 4,419,444 | 12/1983 | Quash | 435/176 |
| 4,563,417 | 1/1986 | Albarella et al. | 935/78 X |
| 4,581,333 | 4/1986 | Kourilsky et al. | 435/7 X |
| 4,618,649 | 10/1986 | Ofstead | 525/378 X |
| 4,652,517 | 3/1987 | Scholl et al. | 935/78 |

OTHER PUBLICATIONS

Hames, B. D. et al. (editor) Nucleic Acid Hybridization a Practical Approach, IRL Press, Oxford, England, 1985, p. 86.
Bio-Rad Bulletin 1110, Bio-Rad Laboratories, 1986, pp. 1-8.
Stuart, W. D. et al., *Proc. Natl. Acad. Sci. U.S.A.*, vol. 78, Jun. 1981, pp. 3751-3754.
Prooijen-Knegt, A. C. et al, *Exp. Cell. Res.*, vol. 141, 1982, pp. 397-407.
Chomczynski, P. et al, *Biochem. Biophys. Res. Comm.*, vol. 122, 1984, pp. 340-344.
Bauman, J. G. J. et al., *J. Histochem. Cytochem.*, vol. 29, 1981, pp. 227-237.
Bolden, A. et al., *J. Virology*, vol. 16, Dec. 1975, pp. 1584-1588.
Sostero, D. et al., *Farmaco Ed. Sci.*, vol. 37, 1982, pp. 74-80.

*Primary Examiner*—Charles F. Warren
*Assistant Examiner*—Jeremy M. Jay
*Attorney, Agent, or Firm*—Andrew L. Klawitter

[57] ABSTRACT

Immobilization of nucleic acids, e.g., DNA and RNA, by contact with a solid support comprising nylon whose amide groups have been partially solvolyzed. Solvolysis of the nylon support can be accomplished by treatment with an alkylating agent such as a trialkyloxonium salt under anhydrous conditions followed by addition of water. The immobilized nucleic acid is particularly useful as an immobilized probe in hybridization assays to detect specific polynucleotide sequences in a test sample.

7 Claims, No Drawings

IMMOBILIZATION OF NUCLEIC ACIDS ON SOLVOLYZED NYLON SUPPORTS

BACKGROUND OF THE INVENTION

This invention relates to means of immobilizing nucleic acids such as DNA and RNA on solid supports. Immobilized nucleic acids find particular use as probes for determining the presence of particular polynucleotide sequences by hybridization with complementary single stranded polynucleotides. Nucleic acid hybridization is useful as an analytical method in the fields of human and veterinary medicine, agriculture, and food science, among others. In particular, the method can be used to detect and identify etiological agents such as bacteria and viruses, to screen microbes for antibiotic resistance, and to detect malignant cells.

Hybridization assays commonly involve the immobilization of either the nucleic acids present in the test sample or the probe nucleic acid. Such solid-phase techniques are concluded with the detection of hybrids formed on the immobilized phase between the probe and complementary sample polynucleotides. By far the most commonly used matrix for immobilization of nucleic acids in these methods has been microporous nitrocellulose membranes. More recently, microporous nylon membranes have become popular because they have better mechanical strength than nitrocellulose. Some manufacturers have introduced positive ionic groups such as quaternary ammonium ions into nylon membranes to improve their wetting proprieties. All of the known nitrocellulose and nylon membranes used to immobilize nucleic acids require high salt to adsorb the polynucleotides to their surface and baking at around 80° C. to permanently fix the adsorbed DNA or RNA.

Detection of resulting immobilized hybrids formed on the solid matrix is conveniently accomplished by the addition of a detectable protein reagent that binds specifically to the hybrids. Normally such protein reagent will comprise an antibody or other binding protein that is specific for binding to a ligand moiety on the probe nucleic acid or to the unique configuration of the hybrid itself. Examples of the former are the detection of probe nucleic acids bearing a biotin or a hapten group by binding of avidin or anti-hapten antibody. Examples of the latter are the use of antibodies selective for DNA.RNA, or RNA.RNA duplexes or intercalated or otherwise antigenically modified duplexes. The specifically binding protein reagent is labeled with a detectable component, commonly an enzyme.

The problem with use of enzyme-labeled, or otherwise detectable, protein reagents to determine hybridization on the conventionally known solid matrices is nonspecific adsorption of such reagent. This nonspecific binding limits the sensitivity of the overall assay procedure. Accordingly, there is a need for better solid matrices for immobilizing nucleic acids, matrices which do not require high salt or baking in order to obtain efficient and stable immobilization. Further, such new matrices are needed particularly for use in hybridization assays, and particularly where resulting hybrids are detected with labeled protein reagents. Also, since hybridization procedures typically require several incubation and washing steps, the known microporous membranes are not amenable to rapid processing because they are fragile and difficult to handle. A solid, more rigid support material would overcome these problems.

SUMMARY OF THE INVENTION

It has now been found that nucleic acids can be efficiently and stably immobilized on a solid support or matrix comprised of nylon having amide groups that have been partially solvolyzed. Solvolysis is the process by which the amide bridges between the monomeric units of nylon are cleaved by treatment with a solvent, usually a protic solvent. As a result, two distinct fragments are formed which terminate in modified or unmodified carboxyl and amine groups respectively. The solvolytic process can involve hydrolysis wherein the terminal functional groups formed are unmodified carboxyl and amine or can involve alcoholysis wherein the terminal groups formed are ester, such as alkyl ester, and amine. Solvolysis of the nylon support is preferably accomplished by treatment with an alkylating agent such as a trialkyloxonium salt under anhydrous conditions followed by addition of water. The precise nature of the interaction between the nucleic acid and the partially solvolyzed nylon support is not understood, however, it is believed that electrostatic and perhaps other noncovalent forces are principally involved.

The present method of immobilizing nucleic acids is characterized by several advantages. There is no need for the presence of high salt concentrations to attain adsorption of nucleic acids to the modified nylon surface. Further, there is no need to bake the adsorbed nucleic acids in order to obtain a stable immobilization to the solid support. A particular advantage where proteinaceous reagents such as enzyme-labeled conjugates are to be used in the detection of hybrids formed on the support is that the modified nylon surface exhibits a very low nonspecific binding of such reagents, enabling more sensitive detection limits to be achieved.

DESCRIPTION OF THE PREFERRED EMBODIMENTS

The extent of solvolysis of the nylon support necessary or desired for a particular nucleic acid immobilization will normally be determined through routine experimentation. The result of solvolysis is the cleavage of amide groups which link the monomeric units in the nylon polymer. Accordingly, the solvolysis will be controlled below that which could destroy or significantly weaken the structural integrity of the nylon support as a whole. Using a bead form of the nylon support as an example, in the normal case it is anticipated that anywhere between 20 and 500 nanomoles of the available amide groups exposed on the surface of a 4.76 mm diameter bead can be solvolyzed. This gives 30 to 700 nanomoles solvolyzable groups per square centimeter assuming the surface to be smooth. Solvolysis of about 150 nanomoles of exposed amide groups on such a 4.76 mm diameter bead has been found to be particularly useful in immobilizing nucleic acids.

It is contemplated that essentially any means can be employed to solvolyze the nylon amide groups to form the useful immobilization support of the present invention. Typically, the solvolysis process will involve conventional acid hydrolysis involving exposure of the nylon support to acids such as hydrochloric, sulfuric, sulfonic, or trichloroacetic acid, or will involve activation of the amide group with an appropriate activating agent under anhydrous conditions followed by addition of water. Activating agents will serve to 0-alkylate the amide to form an imidate salt. The imidates, when treated with water, hydrolyze to form aminocarboalkoxy-substituted nylon. The overall result of alkylation followed by hydrolysis is an alcoholysis, i.e., the equivalent of cleavage with addition of alcohol. Useful alkylating agents include dialkyl sulfates, alkyl triflates, alkyldiphenyl sulfonium salts, alkyl perchlorates, and particularly the trialkyloxonium salts such as the lower alkyl salts, preferably trimethyloxonium and triethyloxonium salts. The salt counteranion will generally be selected from hexachloroantimonate, hexafluorophosphate, and tetrafluoroborate, with the last named counterion being preferred.

A particularly useful general method for effecting solvolysis of the nylon support begins with treatment of the support with a solution of trialkyloxonium salt, e.g., trimethyloxonium tetrafluoroborate, in a nonaqueous solvent such as methylene chloride, carbon tetrachloride or diethyl ether. The incubation will proceed for between about 1½ and about 5 hours, preferably with agitation, with about 3 hours being optimal. The temperature of the reaction can vary widely and is primarily a matter of choice. Room temperature treatments are normally used. The activated support is removed from the nonaqueous solution, optionally followed by a series of washings with the nonaqueous solvent, and contacted with water, preferably a low ionic strength buffer with low nucleophilcity, such as borate, phosphate and carbonate, having a salt concentration of about 0.1 mM or higher and a pH from about 7 to about 10 to prevent acid or base catalyzed hydrolysis of the amide bond. The solvolysis reaction is allowed to proceed for between about 30 minutes and overnight. Preferably, the solvolyzed support will then be washed extensively, even for a period of days to a week in water or buffer. The end product can be stored under water or buffer or in dried form.

The above preferred solvolysis method is understood to yield primarily cleaved fragments with terminal ester and amine groups respectively, such process thus being understood to involve an overall alcoholysis because of the addition of an alcoholic moiety. Minor, or in some cases major, additional products are the carboxyl and amine fragments resulting from simple hydrolysis. All of these end products are considered useful in the nucleic acid immoblization process of the present invention.

The nylon support is generally contemplated to comprise any polyamide, including those composed of $\alpha,\omega$-aminocarboxyl acid monomers as well as those condensed from diamine and dicarbocylic acid monomers. The activation procedure can be applied to any polyamide, regardless of the length of the monomeric units. Aromatic, alkyl, or alkenyl backbones will all give aminocarbalkoxy-substituted nylon. Similarly, the backbone and amide groups can be widely substituted, however, certain functional groups, if present, such as carboxyl, hydroxyl, phenol, and amines, may be modified during alkylation. This can be tolerated so long as the ultimately solvolyzed nylon serves a substantial function to adsorb nucleic acids.

The conformation and general composition of the support can vary as desired for its application to nucleic acid immobilization provided that there are nylon amide groups exposed at its surface for solvolysis and interaction with nucleic acids. The support can be in the form of beads, strips, microtiter wells, test tubes, microporous membranes, and the like. Beads have been found to be particularly advantageous due to their manipulability and high surface area. Particular use has been made of nylon beads having diameters in the range of 1 $\mu M$ to about 1 cm. Supports comprised uniformly or nonuniformly of nylons can be used, or one can use nylon coated on a non-nylon core or base.

The solvolyzed nylon support of the present invention can be used to immobilize nucleic acids in general, including DNA, RNA, and derivatives or modifications thereof, comprising any desired number of bases. Genomic and plasmid nucleic acids as well as restriction fragments thereof and synthetic oligonucleotides can be immobilized according to the present invention.

Typically, a desired nucleic acid or population of nucleic acids will be immobilized on the solvolyzed nylon support by incubation of the support in a buffered solution or dispersion of the nucleic acid. The buffer will preferably be of low sonic strength, normally having a salt concentration of about 0.5 M or less and a pH between about 4 and about 10, with about 7 being preferred. Useful buffers include phosphate, carbonate, Tris, and the like, and will contain nuclease inhibitors such as ethylenediamine tetraacetic acid (EDTA), sodium dodecylsulfate, or aurin tricarboxylic acid. The incubation will proceed for between about 1 and 4 hours to obtain saturation of the binding sites. Shorter incubation times can be used where adsorption of less than saturating amounts of the nucleic acid is acceptable. The temperature of the incubation will be preferably between 20° and 60° C., with slightly elevated temperature being preferred, e.g., 50° C. Upon completion of immobilization, the support will then preferably be icubated in a solution of nonspecific nucleic acid, salmon sperm DNA being well known for this purpose, to saturate unoccupied nucleic acid binding sites.

The immobilized nucleic acid can be used in affinity chromatography and purification methods using single- or double-stranded nucleic acids as the affinity ligand, and will find particular application to hybridization assays to detect a particular polynucleotide sequence in a test sample such as biological fluid. In general, the present means for immobilizing nucleic acids can be used in any hybridization protocol involving the use or formation of a solid-phase polynucleotide.

In typical hybridization assays either the sample nucleic acid or a probe nucleic acid is in an immobilized form when brought into contact with the other for purpose of determining complementarity. The probe will have at least one single stranded base sequence substantially complementary to the sequence of interest. The present method for immobilization will in general be more useful for providing immobilized probe to the assay because extended incubation times can be used in manufacturing or preparing this element without increasing the time necessary for the actual assay.

The formation of resulting hybrids, indicating the presence of the sequence of interest in the sample, can be detected in a number of ways. As is known in the art, the one of the sample nucleic acid and the probe which is not immobilized can be labeled with a detectable marker, such as a radioisotope, fluorescer, chemiluminescer, enzyme, or specifically bindable ligand. The amount of such label that ecomes associated with the nylon support is thus directly related to the degree of hybridization. Alternatively, dual hybridization methods are known wherein a first portion of the sequence of interest hybridizes with immobilized first probe and is detected by hybridization of a mutually exclusive second portion of the sequence of interest with a labeled or otherwise detectable second probe.

A particularly attractive approach to labeling the probe is to incorporate a binding site for a specific binding substance into the probe molecule either by selection of specific nucleotide sequences or by chemical modification of the probe. Examples of binding sites existing in the nucleotide sequence are where the probe comprises a promoter sequence (e.g., lac-promoter, trppromoter) which is bindable by a promoter protein. (e.g., bacteriophage promoters, RNA polymerase), or comprises an operator sequence (e.g., lac operator) which is bindable by a repressor protein (e.g., lac repressor), or comprises rare, antigenic nucleotides or sequences (e.g., 5-bromo or 5-iododeoxyuridine, Z-DNA) which are bindable by specific antibodies (see British patent specification No. 2,125,964). Binding sites introduced by chemical modification of the probe are particularly useful and normally involve linking one member of a specific binding pair to the probe nucleic acid. Useful binding pairs from which to choose include biotin/avidin, haptens and antigens/antibodies, carbohydrates/lectins, enzymes/inhibitors, and the like. Where the binding pair consists of a proteinaceous member and a nonproteinaceous member, it will be preferred to link the nonproteinaceous member to the probe since the proteinaceous member may be unstable under the denaturing conditions of hybridization of the probe. Preferable systems involve linking the probe with a ligand such as biotin or hapten and employing labeled avidin or anti-hapten antibody, respectively. Preparation of useful ligand-labeled probes is known, for example, see European patent publication Nos. 63,879 and 97,373; and PCT Publication No. 83-002,286. I5 Hybridization formats which are particularly useful with the present invention are those involving they use of an immobilized polynucleotide probe and determination of the resulting hybrids by binding of a labeled or otherwise detectable hybrid binding reqent, usually a specific binding protein such as an antibody.selective for the hybrid. Antibodies which have selectivity for particular duplexes compared to single stranded nucleic acids and duplexes of other types include antibodies to DNA.RNA, and RNA.RNA, and to a limited extent DNA.DNA, as well as antibodies to intercalated duplexes.

Antibodies specific for DNA.RNA hybrids can be stimulated by immunogens comprising homopolymeric or heteropolymeric polynucleotide duplexes. Among the possible homopolymer duplexes, particularly preferred is poly(rA).poly(dT) (Kitagawa and Stollar, *Mol. Immunol.*, 19, 413 [1982]). However, in general, heteropolymer duplexes will be preferably used and can be prepared in a variety of ways including transcription of $\phi$X174 virion DNA with RNA polymerase (Nakazato, *Biochem.*, 19, 2835 [1980]). The selected DNA.RNA duplexes are adsorbed to a methylated protein, or otherwise linked to a conventional immunogenic carrier material, such as bovine serum albumin, and injected with a desired host animal [see Stollar *Meth. Enzymol.*, 70:70 (1980)].

Antibodies to RNA.RNA duplexes can be raised against double stranded RNAs from viruses such as reovirus or Fiji disease virus which infects sugar cane, among others. Also, homopolymer duplexes such as poly(rI). poly(rC) or poly(rA). poly(rU), among others, can be used for immunization as above.

Monoclonal antibodies selective for DNA.DNA duplexes are reported in European patent publication No. 135,139.

Antibodies to intercalated duplexes are raised against an immunogen which normally comprises an ionic complex between a cationic protein or protein derivative (e.g., methylated bovine serum albumin) and an anionic intercalated nucleic acid complex. Alternatively, the intercalated complex can be covalently coupled to a carrier protein.

The anti-hybrid antibodies described above will be normally labeled with a detectable group as described above to enable ready determination of hybrids formed on the support of the present invention. Alternatively, the antibody reagent can be detected based on a native property such as its own antigenicity. A labeled anti-(antibody reagent) or protein A will bind to the primary antibody reagent to enable its detection.

The present invention will now be illustrated, but is not intended to be limited, by the following examples.

EXAMPLE

A single stranded DNA probe with a sequence complementary to *E. coli* 23s ribosomal RNA was adsorbed onto solvolyzed nylon beads. The probe was hybridized with *E. coli* 23s RNA and the hybrid was detected with antibody to DNA.RNA hybrids.

Solvolysis of nylon beads

Five hundred 4.8 mm nylon beads (available from Precision Plastic Ball Co., Chicago, IL, USA) were stirred vigorously for 3 hours in 500 mL of anhydrous methylene chloride containing 750 mg trimethyloxonium tetrafluoroborate. The beads were washed immediately with three 100 ml portions of methylene chloride and added to 200 ml of 0.1 M sodium borate buffer, pH 9.5. They were stirred with the buffer for 1.75 hours and then washed for six days with 5 to 7 changes (1 L each) of water. Finally the beads were air dried.

The beads were assayed for primary amine groups by reaction with trinitrobenzene sulfonate (TNBS). One bead was shaken at room temperature for 3 hours with 0.85 ml of 0.1 M $Na_2B_4O_7$ buffer, pH 9.3 containing 1.17 mM TNBS which reacts with amines on the surface and stains the bead yelloworange. Then 150 $\mu$L of 30 mM glycine was added to react with excess TNBS for 30 minutes. A 40 $\mu$L aliquot of the reaction mixture was diluted into 0.96 mL of 0.1 M sodium phosphate buffer, pH 7.0 containing 1.5 mM sodium sulfite and the absorbance at 414 nm was recorded. The total TNBS employed in these reactions was determined with a control prepared as described above except a bead was not included.

A calibration curve is prepared by reacting various levels of glycine (from 0 to 0.8 mM) with 1.6 mM TNBS in the $Na_2B_4O_7$ buffer for 30 minutes. Then 40 $\mu$L aliquots of these reaction mixtures are diluted into 0.96 ml of the phosphate/sulfite solution and the absorbances are recorded. The difference between the total TNBS measured without a bead and the amount of excess TNBS after reaction with a bead gives the molar quantity of amine groups on the bead.

The solvolyzed nylon beads contained an average of 130 nmoles amine/bead.

DNA probe for 23s RNA

An EcoRI/Bgl II fragment from the rrnD operon of *E. coli* coding for 23s RNA was cloned into the M13mp9 vector and the virion DNA was prepared [Jinks-Robertson, et al (1983) Cell 33:865]. RNA contaminating the DNA preparation was destroyed by incubating the DNA in 0.3 M NaOH for 4 hours at 37° C. The alkali was neutralized by addition of 30% acetic acid and the DNA was recovered by precipitation with cold ethanol.

Immobilization of DNA on Solvolyzed Nylon Beads

Fourteen solvolyzed nylon beads were combined with 2.0 mL of sodium phosphate buffer, pH 7.4, containing 1 mM ethylenediamine tetraacetic acid (EDTA) and 28 μL (28 μg) of the DNA probe. The mixture was shaken at 50° C. for 14 hours and then 141 μL of salmon sperm DNA (4.25 mg/mL) was added and the shaking was continued at 50° C. for 4 hours. (The salmon sperm DNA had been treated with 0.3 NaOH for 16 hours at described above for the DNA probe). The beads were placed in 2.0 ml of hybridization solution composed of 40% formamide and 60% aqueous solution containing:
0.2 mg/ml salmon sperm DNA
1 mg/ml polyvinylpyrrolidone
1 mg/ml Ficoll (Pharmacia)
1 mg/ml bovine serum albumin
1.8 M NaCl
10 mM EDTA
0.1 M sodium phosphate buffer pH 7.7
1 mg/ml sodium dodecylsulfate (SDS)
The beads were incubated at 55° C. for 17 hours and washed twice in 2 ml per wash of 1×SSPE, 0.1% SDS (1×SSPE is 10 mM sodium phosphate buffer, pH 7.7, 0.18 M NaCl, 1 mM EDTA).

Preparation of Monoclonal Antibody to DNA.RNA

Preparation of DNA.RNA hybrid - The hybrid was prepared by transcription of φX174 virion DNA with DNA dependent RNA polymerase from E. coli. The procedure was described by Nakazato (1980) Biochem. 19:2835.

Preparation of methylated thyroglobulin-Bovine thyroglobulin (Sigma Chemical Co., St. Louis, MO, USA), 100 mg, was combined with 10 ml of anhydrous methanol and 400 μL of 2.5 M HCl in methanol. The mixture was allowed to react for 5 days on a rotary mixer at room temperature. The precipitate was collected by centrifugation and washed twice with methanol and twice with ethanol. Then it was dried under vacuum overnight.

Immunization of mice—One hundred fifty micrograms of DNA.RNA hybrid in 250 μof 20 mM Trishydrochloride buffer, pH 7.4, 1 mM EDTA was combined with 150 μg of methylated thyroglobulin in 50 μl water. A precipitate formed and 2.5 ml of the Tris buffer was added. The entire mixture was emulsified with an equal volume of Freunds adjuvant. BALB/c mice were each immunized with 0.5 ml of the suspension. Booster immunizations were given 3 weeks later and at one week intervals thereafter. Blood was taken at two week intervals beginning one week after the first boost.

Antibody titers in the serums were measured by an enzyme labeled immunosorbent assay method. Immulon II (Dynateck, Alexandria, VA, USA) microtiter wells were coated with DNA.RNA by placing 50 μl of a 5 μg/ml solution in each well. The DNA.RNA was in 0.015 M sodium citrate buffer, pH 6.8, containing 0.15 M NaCl. When the solutions had stood at room temperature for 2 hours, the wells were washed with 0.02 M sodium phosphate buffer, pH 7.4, containing 5 mg bovine serum albumin/mL and 0.5% Tween 20 detergent (v/v). Appropriate dilutions of antiserums were added to the wells to allow binding of the antibodies to the immobilized DNA.RNA. Then the bound antibodies were detected with enzyme labeled anti-mouse IgG by well-known procedures. Spleen cells from a mouse with a high serum titer to DNA.RNA but low titer to single stranded DNA were fused with myeloma cells to produce hybridomas (Stuart et al [1981]Proc. Natl. Acad. Sci. USA, 78:3751; Galfre and Milstein [1981]Met. in Enzymol., 73:1;) e.g., the cell line deposited with the American Type Culture Collection, Rockville, MD, USA as ATCC HB 8730.

Cloned hybridomas are grown intraperitoneally in mice to produce adequate quantities of antibody for further work. Antibody was isolated from the ascites fluid by anion-exchange high pressure liquid chromatography.

Hybridization Assay for 23s RNA

A series of hybridizations were conducted in 150 μl of hybridization solution containing various levels of E. coli 23s RNA. One bead with the immobilized DNA probe was included in each reaction and the mixtures were incubated at 55° C. for 21 hours. Then the beads were rinsed in 0.5 ml of 1 ×SSPE, 0.1% SDS and incubated at 55° C. for 30 minutes in 0.5 ml of this solution. They were rinsed once more and the amounts of DNA.RNA hybrid formed were determined by immunoassay.

The beads were shaken individually for 30 minutes at room temperature in 50 μL of 0.02 M sodium phosphate, pH 7.4, 0.15 M NaCl, 0.5% (w/v) bovine serum albumin, 0.5% (v/v) Tween 20, 1 mM EDTA (PBS/BSA/Tween/EDTA). Then 100 μL of 1 μg anti-DNA.RNA/ml in PBS/BSA/Tween/EDTA was added and the shaking was continued for 30 minutes. The beads were rinsed twice (0.5 mL each) with 50 mM sodium phosphate buffer, pH 7.4, 0.5% (v/v) Tween, 0.5% (w/v) BSA, 1.0 mM $MgCl_2$ (phosphate/Tween/-BSA/$MgCl_2$).

Each bead was shaken for 1 hour with 150 μL of β-galactosidase labeled antimouse IgG (Amersham, Chicago, IL, USA) diluted 500-fold in the phosphate/Tween/BSA/$MgCl_2$. The beads were washed twice for 5 minutes each by shaking in 0.5 ml of phosphate/Tween/BSA/$MgCl_2$ containing 0.5 M NaCl.

Bound β-galactosidase label was measured by incubating each bead at 25° C. for 30 minutes in 250 μL of 0.8 mM 7-β-galactosyl-3-[3-dimethylaminopropylcarboxamide]-coumarin (Worah et al. [1981]Clin. Chem., 27:673) in 50 mM sodium phosphate buffer, pH 7.4, 5mM $MgCl_2$. Then 1.5 ml of the phosphate buffer was added and the fluorescence was recorded using 405 nm for excitation and 450 for emission.

| 23s RNA added to hybridization (pg/assay) | Fluorescence (average of duplicates) |
| --- | --- |
| 0 | 697 |
| 30 | 1240 |
| 100 | 2500 |

The enzyme activity increased as the 23 s RNA in the hybridization solution increased indicating the presence of hybrids between sample RNA and the probe DNA immobilized to the hydrolyzed nylon beads.

The bead without 23s RNA added to the hybridization mixture bond nonspecifically 0.15% of β-galactosidase-labeled anti-mouse IgG. Similar experiments with nitrocellulose microporous membranes and β-galactosidase labeled binding proteins give 0.3 up to 2.0% nonspecific binding.

What is claimed is:

1. A method for immobilizing a nucleic acid consisting essentially of the step of contacting the nucleic acid with a solid support consisting essentially of nylon whose amide groups have been partially solvolyzed whereby said nucleic acid becomes bound to the solid support by noncovalent bonds.

2. The method of claim 1 wherein the nylon is treated with an alkylating agent under anhydrous conditions and thereafter contacted with water.

3. The method of claim 2 wherein the activating agent is a trialkyloxonium salt.

4. The method of claim 1 wherein the nucleic acid to be immobilized has a predetermined base sequence and after, such nucleic acid has been bound to the nylon support such support is contacted with a nonspecific nucleic acid to saturate any remaining nucleic acid binding sites on such support.

5. The method of claim 1 wherein the solid support is in the shape of a bead.

6. The method of claim 1 wherein the nucleic acid is DNA.

7. The method of claim 1 wherein the nucleic acid is RNA.

* * * * *